United States Patent [19]

Trummlitz et al.

[11] Patent Number: 4,533,664
[45] Date of Patent: Aug. 6, 1985

[54] ANTITHROMBOTIC N-(6-CHLORO-PYRAZIN-2-YL)-4-HYDROXY-2H-1,2-BENZOTHIAZINE-3-CARBOXAMIDE-1,1-DIOXIDE DERIVATIVES, COMPOSITION, AND METHOD OF USE

[75] Inventors: Günter Trummlitz, Warthausen; Wolfhard Engel, Biberach; Ernst Seeger, Biberach; Walter Haarmann, Biberach, all of Fed. Rep. of Germany

[73] Assignee: Dr. Karl Thomae Gesellschaft mit beschränkter Haftung, Biberach/Riss, Fed. Rep. of Germany

[21] Appl. No.: 537,592

[22] Filed: Sep. 30, 1983

[30] Foreign Application Priority Data

Oct. 9, 1982 [DE] Fed. Rep. of Germany ....... 3237473

[51] Int. Cl.$^3$ .................... A61K 31/38; C07D 417/02
[52] U.S. Cl. ........................................ 514/225; 544/49
[58] Field of Search .................... 544/49; 424/246; 514/225

[56] References Cited

U.S. PATENT DOCUMENTS 4,233,299 11/1980 Trummlitz et al. ............... 544/49

FOREIGN PATENT DOCUMENTS 0070888 1/1982 Japan ..................... 544/49

OTHER PUBLICATIONS

Carty et al., Index Chem.: C.A.S., vol. 77, Issue 859, 1980, (296563).

*Primary Examiner*—Henry R. Jiles
*Assistant Examiner*—J. G. Mullins
*Attorney, Agent, or Firm*—Hammond & Littell, Weissenberger & Dippert

[57] ABSTRACT

Compounds of the formula

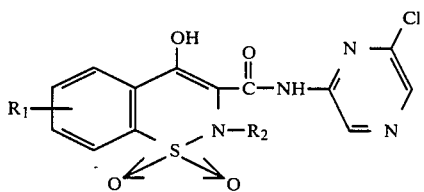

wherein
  $R_1$ is hydrogen, methyl, methoxy, fluorine or chlorine; and
  $R_2$ is hydrogen, methyl, ethyl or n-propyl;
and non-toxic, pharmacologically acceptable salts thereof formed with an inorganic or organic base. The compounds as well as the salts are useful as antithrombotics.

5 Claims, No Drawings

ANTITHROMBOTIC N-(6-CHLORO-PYRAZIN-2-YL)-4-HYDROXY-2H-1,2-BENZOTHIAZINE-3-CARBOXAMIDE-1,1-DIOXIDE DERIVATIVES, COMPOSITION, AND METHOD OF USE

This invention relates to novel N-(6-chloro-pyrazin-2-yl)-4-hydroxy-2H-1,2-benzothiazine-3-carboxamide-1,1-dioxides and non-toxic salts thereof, to methods of preparing these compounds, to pharmaceutical compositions containing them as active ingredients, and to a method of using them as antithrombotics.

THE PRIOR ART German Offenlegungsschriften Nos. 1,943,265 and 2,756,113 disclose 3,4-dihydro-2H-1,2-benzothiazine-1,1-dioxides and 4-hydroxy-2H-1,2-benzothiazine-3-carboxamide-1,1-dioxides, respectively; the compounds are primarily useful as antiphlogistics.

DESCRIPTION OF THE INVENTION

More particularly, the present invention relates to a novel class of compounds represented by the formula

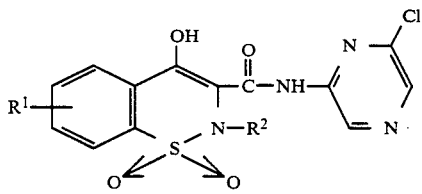

wherein
$R_1$ is hydrogen, methyl, methoxy, fluorine or chlorine; and
$R_2$ is hydrogen, methyl, ethyl or n-propyl;
and non-toxic, pharmacologically acceptable salts thereof formed with an inorganic or organic base.

The compounds embraced by formula I may be prepared by the following methods:

Method A

All of the compounds embraced by formula I can be prepared by reacting a 4-hydroxy-2H-1,2-benzothiazine-1,1-dioxide-3-carboxylic acid derivative of the formula

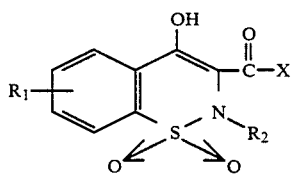

wherein
X is a nucleophilically exchangeable substituent, such as alkoxy of 1 to 8 carbon atoms, phenyl(alkoxy of 1 to 4 carbon atoms), phenoxy, halogen, amino, (alkyl of 1 to 8 carbon atoms)amino, (cycloalkyl of 3 to 10 carbon atoms)amino, phenyl(alkyl of 1 to 4 carbon atoms)amino or anilino; and
$R_1$ and $R_2$ have the meanings previously defined, with 2-amino-6-chloro-pyrazine of the formula

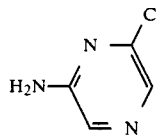

The reaction of a carboxylic acid ester of the formula II with 2-amino-6-chloro-pyrazine is effected in a suitable inert organic solvent, for example in an aromatic hydrocarbon such as benzene, toluene, xylene, chlorobenzene, o-dichlorobenzene or tetrahydronaphthalene; in dimethylformamide, dimethylacetamide or dimethylsulfoxide; in hexamethylphosphoric acid triamide; in ethers, such as dimethoxyethane, diethyleneglycol dimethyl ether or diphenyl ether; or in an excess of the pyrazine of the formula III. The reaction is carried out at a temperature of 60° to 200° C., or between 20° and 180° C. if X in formula II is an alkoxy group. Preferably, the reaction is carried out in toluene or xylene at the boiling point of the reaction mixture and, if X in formula II is an alkoxy, phenylalkoxy or phenyloxy group, the alcohol or phenol formed during the reaction is removed by azeotropic distillation or by refluxing, for example using a Soxhlet extractor equipped with a molecular sieve. The reaction product crystallizes directly out of the reaction mixture or is precipitated by adding water, if a water-miscible solvent is used. If X in formula II is amino or amino substituted as described above, it is advantageous to add a catalytic quantity of p-toluenesulfonic acid to the reaction mixture and to use the pyrazine of the formula III in excess. Again, the product often crystallizes directly out of the reaction mixture, but in any case can always be obtained by evaporating the solvent; however, if a water-miscible solvent is used, the product may also be precipitated by adding water.

Method B

A compound of the formula I wherein $R_2$ is methyl, ethyl or n-propyl and $R_1$ has the meanings previously defined may also be obtained by reacting a 4-hydroxy-2H-1,2-benzothiazine- 3-carboxamide-1,1-dioxide of the formula

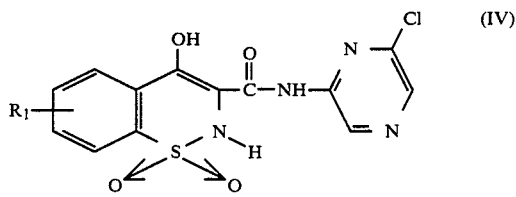

wherein
$R_1$ has the meanings previously defined,
with an alkyl halide of the formula $R_2'$—Hal     (V)

wherein
Hal is halogen, and
$R_2'$ is methyl, ethyl or n-propyl,
in the presence of a base.

The base may be an alkali metal or alkaline earth metal hydroxide such as sodium, potassium or barium hydroxide; or an alkali metal or alkaline earth metal carbonate such as sodium or potassium carbonate; an alkali metal or alkaline earth metal alkoxide such as sodium methoxide, potassium ethoxide or potassium tert.butoxide; or a tertiary amine such as triethylamine, if the reaction is performed in an aqueous medium, in an alcoholic medium such as in methanol, ethanol, n-propanol, isopropanol, or in a mixture of these solvents. If an alkali metal alkoxide is used, it is best to perform the reaction in the corresponding alcoholic medium.

The alkyl halide, preferably an alkyl bromide or iodide, is advantageously added directly to the other components in the reaction mixture in an alcoholic solution; if methyl bromide is used, the reaction is carried out in a closed vessel. Other solvents which may be used are dimethylformamide, dimethylacetamide, dimethylsulfoxide and hexamethylphosphoric acid triamide.

If an alkali metal or alkaline earth metal carbonate is used as the base, an aliphatic ketone such as acetone may also be used as the solvent.

If the reaction is carried out in an aprotic organic solvent such as benzene or another aromatic hydrocarbon, tetrahydrofuran or another open-chained or cyclic ether, an alkali metal hydride or alkaline earth metal hydride such as sodium hydride may also be used as the base. However, the alkyl halide is not added until the alkali metal hydride or alkaline earth metal hydride has reacted completely with the starting compound of the formula IV. The reaction temperature is from 0° to 80° C.

In some cases it is advisable to protect the 4-hydroxy group in compounds of the formula II or IV by means of a protective group before the two methods described above are carried out, and then to remove this protective group again after the reaction is completed. Thus, for example, it is advantageous to etherify the 4-hydroxy groups; these hydroxy groups are converted in known manner into the corresponding alkoxy or phenylalkoxy groups, for example into alkoxy groups with 1 to 8 carbon atoms or phenylalkoxy groups with a total of 7 to 10 carbon atoms, and after the reaction these protective groups are split off again, for example by heating them in an inorganic acid such as hydrobromic acid at temperatures of up to 100° C., or by adding a boron trihalide such as boron tribromide or boron trichloride in an inert solvent such as a chlorinated hydrocarbon at temperatures between −80° and +80° C.

The compounds of the formula I are acidic and therefore form salts with inorganic or organic bases. Examples of non-toxic, pharmacologically acceptable salts are those formed with an alkali metal alkoxide, an alkali metal hydroxide, an alkaline earth metal hydroxide, a trialkylammonium hydroxide or an alkylamine, but preferably with an aminopolyalcohol such as N-methyl-D-glucamine.

The ester starting compounds of the formula II, that is, those wherein X is alkoxy, phenylalkoxy or phenoxy, are generally known and may be prepared, for example, according to German Offenlegungsschrift No. 1,943,265 (see also U.S. Pat. No. 3,591,584); thus, for example, using the known 3-oxo-1,2-benzisothiazole-2(3H)acetic acid ester-1,1-dioxides (Chem. Berichte 30, 1267 [1897]) as starting materials, an alkali metal alkoxide such as sodium ethoxide in an organic polar solvent such as dimethylsulfoxide or dimethylformamide is added thereto. A rearrangement reaction sets in, and after acidification the corresponding ester of the formula II wherein $R_2$ is hydrogen is obtained. If it is desired to introduce the other groups mentioned for $R_2$ above into the 2-position of this ester, this is most advantageously done by using an alkyl halide, preferably an alkyl iodide; the alkylation is effected in the presence of a base.

The starting compounds of the formula II wherein X is amino or substituted amino are known from the literature; they may be prepared, for example, as described in German Offenlegungsschrift No. 1,943,265 (cf. also U.S. Pat. No. 3,591,584) from a 4-hydroxy-2H-1,2-benzothiazine-3-carboxylic acid ester-1,1-dioxide of the formula II by reacting the same with an amine of the formula $NH_2$—$R_4$ wherein $R_4$ is hydrogen, alkyl of 1 to 8 carbon atoms, cycloalkyl of 3 to 10 carbon atoms, phenylalkyl of a total of 7 to 10 carbon atoms or phenyl, in an inert solvent such as dimethylsulfoxide or tert.butanol, at temperatures between 20° and 200° C.

The starting compounds of the formula II wherein X is halogen are obtained, for example, by reacting a corresponding 4-hydroxy- or 4-alkoxy-2H-1,2-benzothiazine-3-carboxylic acid-1,1-dioxide with a thionyl halide in a solvent such as benzene and/or dimethylformamide at temperatures up to the reflux temperature of the reaction mixture.

The compound of the formula III is also known from the literature.

The starting compounds of the formula IV are prepared, for example, from a 4-hydroxy-2H-1,2-benzothiazine-3-carboxylic acid ester-1,1-dioxide of the formula II wherein $R_2$ is hydrogen, by reacting the same with 2-amino-6-chloropyrazine in a suitable inert organic solvent at temperatures between 20° and 180° C.

The following examples illustrate the present invention and will enable others skilled in the art to understand it more completely. It should be understood, however, that the invention is not limited solely to the particular examples given below.

EXAMPLE 1

N-(6-Chloro-pyrazin-2-yl)-4-hydroxy-2-methyl-2H-1,2-benzothiazine-3-carboxamide-1,1-dioxide A mixture of 9.0 g (33 mmols) of methyl 4-hydroxy-2-methyl-2H-1,2-benzothiazine-3-carboxylate-1,1-dioxide, 4.36 g (33 mmols) of 2-amino-6-chloro-pyrazine and 1200 ml of xylene was refluxed for 24 hours in a nitrogen atmosphere. The methanol formed by the reaction was removed with the aid of a 4 Å molecular sieve arranged in a Soxhlet attachment. After cooling and standing overnight, the crystals were filtered off and recrystallized from dioxane. 7.91 g (64% of theory) of N-(6-chloro-pyrazin-2-yl)-4-hydroxy-2-methyl-2H-1,2-benzothiazine-3-carboxamide-1,1-dioxide were obtained.

Melting point: 278°–279° C. (decomposition).

IR (KBr): 1655 cm$^{-1}$ (CO amide).

1H-NMR ([D$_6$]-DMSO): $\delta = 11.70$ (br.s,1,OH, exchangeable with CD$_3$OD; 9.3 (s,1,3'-H); 8.6 (s,1,5'-H); 8.1–7.8 (m,4,5-H to 8H); 2.85 (s,3,N-CH$_3$).

MS: M+ 366 m/e.

$C_{14}H_{11}ClN_4O_4S$ (366.79):

Calc.: C—45.84%; H—3.03%; N—15.28%; Cl—9.67%; S—8.74%.

Found: C—46.08%; H—3.04%; N—15.31%; Cl—9.62%; S—8.64%.

EXAMPLE 2

N-(6-Chloro-pyrazin-2-yl)-4-hydroxy-6-methoxy-2-methyl-2H-1,2-benzothiazine-3-carboxamide-1,1-dioxide A mixture of 5.2 g (17 mmols) of methyl 4-hydroxy-6-methoxy-2-methyl-2H-1,2-benzothiazine-3-carboxylate-1,1-dioxide, 2.5 g (19 mmols) of 2-amino-6-chloropyrazine and 200 ml of xylene was refluxed for 24 hours. The methanol formed during the reaction was removed with the aid of a 4 Å molecular sieve arranged in a Soxhlet attachment. After cooling to room temperature, the reaction mixture was filtered, and the residue was recrystallized from tetrahydrofuran.

4.9 g (73% of theory) of N-(6-chloro-pyrazin-2-yl)-4-hydroxy-6-methoxy-2-methyl-2H-1,2-benzothiazine-3-carboxamide-1,1-dioxide were obtained.

Melting point: 289°–291° C.

1H-NMR (CDCl$^3$+d-TFA): $\delta$=9.45 (s, 1,3'-H); 8.55 (s, 1,5'-H); 7.93 (d,1,J=10 Hz, 8-H); 7.62 (d,1,J=3 Hz, 5-H); 7.35 (dd,1,J$_1$=10 Hz, J$_2$=3 Hz, 7-H); 4.00 (s,3, OCH$_3$); 3.00 (s,3, NCH$_3$).

$C_{15}H_{13}ClN_4O_5S$ (396.83):
Calc.: C—45.40%; H—3.30%; N—14.12%; Cl—8.93%; S—8.08%.
Found: C—45.70%; H—3.58%; N—14.00%; Cl—9.08%; S—8.33%.

EXAMPLE 3

N-(6-Chloro-pyrazin-2-yl)-2,6-dimethyl-4-hydroxy-2H-1,2-benzothiazine-3-carboxamide-1,1-dioxide 2.0 g (7 mmols) of methyl 2,6-dimethyl-4-hydroxy-2H-1,2-benzothiazine-3-carboxylate-1,1-dioxide and 1.1 g (8.4 mmols) of 2-amino-6-chloro-pyrazine were reacted in 150 ml of xylene analogous to Example 2, and the reaction product was isolated and recrystallized from ethylene chloride.

2.1 g (79% of theory) of N-(6-chloro-pyrazin-2-yl)-2,6-dimethyl-4-hydroxy-2H-1,2-benzothiazine-3-carboxamide-1,1-dioxide were obtained.

Melting point: 296°–298° C.

1H-NMR (CDCl$_3$+d-TFA): $\delta$=9.55 (s, 1,3'-H); 8.55 (s, 1,5'-H); 8.05–7.55 (m, 3,5-H, 7-H, 8-H); 3.00 (s,3,N-CH$_3$); 2.60 (s,3,CH$_3$).

$C_{15}H_{13}ClN_4O_4S$ (380.83):
Calc.: C—47.31%; H—3.44%; N—14.71%; Cl—9.31%; S—8.42%.
Found: C—47.30%; H—3.56%; N—14.67%; Cl—9.44%; S—8.61%.

EXAMPLE 4

N-(6-Chloro-pyrazin-2-yl)-2,7-dimethyl-4-hydroxy-2H-1,2-benzothiazine-3-carboxamide-1,1-dioxide 7.5 g (26 mmols) of methyl 2,7-dimethyl-4-hydroxy-2H-1,2-benzothiazine-3-carboxylate-1,1-dioxide and 4.36 g (33 mmols) of 2-amino-6-chloro-pyrazine were reacted in 40 ml of xylene and worked up analogous to Example 2.

7.2 g (73% of theory) of N-(6-chloro-pyrazin-2-yl)-2,7-dimethyl-4-hydroxy-2H-1,2-benzothiazine-3-carboxamide-1,1-dioxide were obtained.

IR (KBr): 1645 cm$^{-1}$ (CO amide).

$C_{15}H_{13}ClN_4O_4S$ (380.83):
Calc.: C—47.31%; H—3.44%; N—14.71%; Cl—9.31%; S—8.42%.
Found: C—47.09%; H—3.52%; N—14.70%; Cl—9.45%; S—8.30%.

Example 5

N-(6-Chloro-pyrazin-2-yl)-7-fluoro-4-hydroxy-2-methyl-2H-1,2-benzothiazine-3-carboxamide-1,1-dioxide 4.1 g (15 mmols) of methyl 7-fluoro-4-hydroxy-2-methyl-2H-1,2-benzothiazine-3-carboxylate-1,1-dioxide and 2.3 g (18 mmols) of 2-amino-6-chloropyrazine were reacted in 200 ml of xylene analogous to Example 2 and worked up in analogy thereto.

3.8 g (66% of theory) of N-(6-chloro-pyrazin-2-yl)-7-fluoro-4-hydroxy-2-methyl-2H-1,2-benzothiazine-3-carboxamide-1,1-dioxide were obtained.

IR (KBr): 1645 cm$^{-1}$ (CO amide).

$C_{14}H_{10}ClFN_4O_4S$ (384.78):
Calc.: C—43.70%; H—2.62%; N—14.56%; S—8.33%.
Found: C—43.84%; H—2.89%; N—14.39%; S—8.30%.

Example 6

6-Chloro-N-(6-chloro-pyrazin-2-yl)-4-hydroxy-2-methyl-2H-1,2-benzothiazine-3-carboxamide-1,1-dioxide 3.04 (10 mmols) of methyl 6-chloro-4-hydroxy-2-methyl-2H-1,2-benzothiazine-3-carboxylate-1,1-dioxide and 1.5 g (12 mmols) of 2-amino-6-chloro-pyrazine were reacted in 150 ml of xylene analogous to Example 2. 3.2 g (80% of theory) of 6-chloro-N-(6-chloro-pyrazin-2-yl)-4-hydroxy-2-methyl-2H-1,2-benzothiazine-3-carboxamide-1,1-dioxide were obtained.

Melting point: 283°–284° C. (from dioxane).

$C_{14}H_{10}Cl_2N_4O_4S$ (401.23):
Calc.: C—41.91%; H—2.51%; N—13.96%; Cl—17.67%; S—7.99%.
Found: C—42.05%; H—2.62%; N—14.09%; Cl—17.54%; S—7.80%.

EXAMPLE 7

N-(6-Chloro-pyrazin-2-yl)-4-hydroxy-2H-1,2-benzothiazine-3-carboxamide-1,1-dioxide A mixture of 5.1 g (20 mmols) of methyl 4-hydroxy-2H-1,2-benzothiazine-3-carboxylate-1,1-dioxide, 3.0 g (23 mmols) of 2-amino-6-chloropyrazine and 400 ml of xylene was refluxed for 12 hours in a nitrogen atmosphere. The methanol formed by the reaction was removed with the aid of a 4 Å molecular sieve arranged in a Soxhlet attachment. After cooling, the reaction mixture was concentrated by evaporation, and the residue was purified by chromatography on a silicagel column, yielding 2.3 g (33% of theory) of N-(6-chloro-pyrazin-2-yl)-4-hydroxy-2H-1,2-benzothiazine-3-carboxamide-1,1-dioxide.

Melting point: 234°–235° C. (from ethanol).

$C_{13}H_9ClN_4O_4S$ (352.76):
Calc.: C—44.26%; H—2.57%; N—15.88%; Cl—10.05%; S—9.09%.
Found: C—44.02%; H—2.65%; N—15.92%; Cl—10.10%; S—9.24%.

EXAMPLE 8

N-(6-Chloro-pyrazin-2-yl)-2-ethyl-4-hydroxy-2H-1,2-benzothiazine-3-carboxamide-1,1-dioxide 8.5 g (30 mmols) of methyl 2-ethyl-4-hydroxy-2H-1,2-benzothiazine-3-carboxylate-1,1-dioxide and 3.9 g (30 mmols) of 2-amino-6-chloro-pyrazine were reacted in 600 ml of xylene and worked up analogous to Example 1, yielding 7.3 g (64% of theory) of N-(6-chloro-pyrazin-2-yl)-2-ethyl-4-hydroxy-2H-1,2-benzothiazine-3-carboxamide-1,1-dioxide.

Melting point: 233°–235° C. (from xylene).
$C_{15}H_{13}ClN_4O_4S$ (380.83):
Calc.: C—47.31%; H—3.44%; Cl—9.31%; N—14.71%; S—8.42%.
Found: C—47.42%; H—3.44%; Cl—9.50%; N—14.62%; S—8.51%.

EXAMPLE 9

N-(6-Chloro-pyrazin-2-yl)-4-hydroxy-2-n-propyl-2H-1,2-benzothiazine-3-carboxamide-1,1-dioxide 2.97 g (10 mmols) of methyl 2-n-propyl-4-hydroxy-2H-1,2-benzothiazine-3-carboxylate-1,1-dioxide and 1.3 g (10 mmols) of 2-amino-6-chloro-pyrazine were reacted in 150 ml of xylene analogous to Example 1, yielding 2.05 g (52% of theory) of N-(6-chloro-pyrazin-2-yl)-4-hydroxy-2-n-propyl-2H-1,2-benzothiazine-3-carboxamide-1,1-dioxide.
$C_{16}H_{15}ClN_4O_4S$ (394.86):
Calc.: C—48.67%; H—3.83%; Cl—8.98%; N—14.19%; S—8.12%.
Found: C—48.91%; H—3.79%; Cl—8.90%; N—14.18%; S—8.03%.

EXAMPLE 10

(a) Sodium salt of N-(6-chloro-pyrazin-2-yl)-4-hydroxy-2-methyl-2H-1,2-benzothiazine-3-carboxamide-1,1-dioxide 1 g (2.7 mmols) of N-(6-chloro-pyrazin-2-yl)-4-hydroxy-2-methyl-2H-1,2-benzothiazine-3-carboxamide-1,1-dioxide were dissolved in a mixture of 2.7 ml of 1N sodium hydroxide and 50 ml of ethanol. The solution was concentrated by evaporation, and the residue was recrystallized from ethyl acetate/ethylene chloride (1:1), yielding 900 mg (86% of theory) of the sodium salt.

Melting point: 214°–215° C.
$C_{14}H_{10}ClN_4NaO_4S$ (388.78):
Calc.: C—43.25%; H—2.59%; Cl—9.12%; N—14.41%; S—8.25%.
Found: C—42.90%; H—2.84%; Cl—9.14%; N—14.09%; S—8.10%.

(b) Potassium salt of N-(6-chloro-pyrazin-2-yl)-4-hydroxy-2-methyl-2H-1,2-benzothiazine-3-carboxamide-1,1-dioxide 36.4 g of N-(6-chloro-pyrazin-2-yl)-4-hydroxy-2-methyl-2H-1,2-benzothiazine-3-carboxamide-1,1-dioxide were suspended in 0.5 liters of ethanol, and the suspension was mixed with 99.2 ml of 1N potassium hydroxide. The resulting solution was evaporated to dryness, the residue was dissolved by refluxing in a mixture of 800 ml of tetrahydrofuran and 50 ml of water, and the solution was filtered while hot. After cooling to room temperature, the solution was cooled overnight in a refrigerator at 0° C., and the precipitate formed thereby was filtered off. The precipitate was washed in a suction filter with copious amounts of ether and then dried, first for 1 hour in a desiccator over paraffin and then for 2 hours in a drying chamber at 60° C.

Melting point: 234°–236° C. (decomposition).
$C_{14}H_{10}ClN_4KO_4S \times H_2O$ (422.90):
Calc.: C—39.76%; H—2.86%; Cl—8.76%; N—13.84%; S—7.92%.
Found: C—39.84%; H—2.80%; Cl—8.39%; N—13.43%; S—7.68%.

EXAMPLE 11

N-(6-Chloro-pyrazin-2-yl)-4-hydroxy-2-methyl-2H-1,2-benzothiazine-3-carboxamide-1,1-dioxide This compound was prepared from ethyl 4-hydroxy-2-methyl-2H-1,2-benzothiazine-3-carboxylate-1,1-dioxide and 2-amino-6-chloro-pyrazine analogous to Example 1.

Yield: 60% of theory.
Melting point: 278–279° C. (decomposition).
$C_{14}H_{11}ClN_4O_4S$ (366.79):
Calc.: C—45.84%; H—3.03%; Cl—9.67%; N—15.28%; S—8.74%. Found: C—45.91%; H—3.09%; Cl—9.60%; N—15.00%; S—8.78%.

EXAMPLE 12

N-(6-Chloro-pyrazin-2-yl)-4-hydroxy-2-methyl-2H-1,2-benzothiazine-3-carboxamide-1,1-dioxide This compound was prepared from methyl 4-hydroxy-2-[methyl-2H-1,2-benzothiazine-3-carboxylate-1,1-dioxide and 2-amino-6-chloro-pyrazine analogous to Example 1, but using o-dichlorobenzene as the solvent.

Yield: 48% of theory.
Melting point: 278°–279° C. (decomposition).
$C_{14}H_{11}ClN_4O_4S$ (366.79):
Calc.: C—45.84%; H—3.03%; Cl—9.67%; N—15.28%; S—8.74%.
Found: C—45.91%; H—3.09%; Cl—9.60%; N—15.00%; S—8.78%.

EXAMPLE 13

N-(6-Chloro-pyrazin-2-yl)-4-hydroxy-2-methyl-2H-1,2-benzothiazine-3-carboxamide-1,1-dioxide 1.23 g (4.5 mmols) of 4-hydroxy-2-methyl-2H-1,2-benzothiazine-3-carboxylic acid chloride-1,1-dioxide were dissolved in 10 ml of dimethylformamide, and 1.3 g (10 mmols) of 2-amino-6-chloro-pyrazine were added in portions thereto. The reaction mixture was stirred for 24 hours at room temperature and was then mixed with 40 ml of water. The aqueous mixture was stirred for 20 minutes at room temperature, and then the precipitate which had formed was filtered off, washed and dried. Recrystallization from dioxane yielded 0.4 g (24% of theory) of N-(6-chloro-pyrazin-2-yl)-4-hydroxy-2-methyl-2H-1,2-benzothiazine-3-carboxamide-1,1-dioxide.

Melting point: 278°–279° C. (decomposition).
$C_{14}H_{11}ClN_4O_4S$ (366.79):
Calc.: C—45.84%; H—3.03%; Cl—9.67%; N—15.28%; S—8.74%.
Found: C—46.02%; H—3.00%; Cl—9.72%; N—15.42%; S—8.84%.

EXAMPLE 14

N-(6-Chloro-pyrazin-2-yl)-4-hydroxy-2-methyl-2H-1,2-benzothiazine-3-carboxamide-1,1-dioxide 1.0 g (3 mmols) of 4-hydroxy-2-methyl-N-phenyl-2H-1,2-benzothiazine-3-carboxamide-1,1-dioxide were refluxed with 1.3 g (10 mmols) of 2-amino-6-chloro-pyrazine and 0.1 g of p-toluenesulfonic acid in 250 ml of xylene for 72 hours. After cooling, the reaction mixture was washed with 2N hydrochloric acid and then with water, then dried and concentrated by evaporation in vacuo. The residue was purified by column chromatography (Merck silicagel 60; particle size: 0.2–0.5 mm; eluant: chloroform/ethanol 90:10) and yielded 0.25 g (23% of theory) of N-(6-chloro-pyrazin-2-yl)-4-hydroxy-2-methyl-2H-1,2-benzothiazine-3-carboxamide-1,1-dioxide.

Melting point: 278°–279° C. (decomposition; from dioxane).

$C_{14}H_{11}ClN_4O_4S$ (366.79):
Calc. C—45.84%; H—3.03%; Cl—9.67%; N—15.28%; S—8.74%.
Found: C—45.50%; H—3.09%; Cl—9.70%; N—15.20%; S—8.79%.

EXAMPLE 15

(a)
N-(6-Chloro-pyrazin-2-yl)-4-hydroxy-2-methyl-2H-1,2-benzothiazine-3-carboxamide-1,1-dioxide This compound was prepared from 4-hydroxy-2-methyl-2H-1,2-benzothiazine-3-carboxamide-1,1-dioxide, 2-amino-6-chloro-pyrazine and p-toluenesulfonic acid analogous to Example 14.
Yield: 64% of theory.
Melting point: 278°–279° C. (from dioxane).

(b)
N-(6-Chloro-pyrazin-2-yl)-4-hydroxy-2-methyl-2H-1,2-benzothiazine-3-carboxamide-1,1-dioxide This compound was prepared from 4-hydroxy-2-methyl-N-methyl-2H-1,2-benzothiazine-3-carboxamide-1,1-dioxide, 2-amino-6-chloro-pyrazine and p-toluenesulfonic acid analogous to Example 14.
Yield: 68% of theory.
Melting point: 278°–279° C. (decomposition).
$C_{14}H_{11}ClN_4O_4S$ (366.79):
Calc.: C—45.84%; H—3.03%; Cl—9.67%; N—15.28%; S—8.74%.
Found: C—45.61%; H—3.14%; Cl—9.71%; N—15.02%; S—8.58%.

(c)
N-(6-Chloro-pyrazin-2-yl)-4-hydroxy-2-methyl-2H-1,2-benzothiazine-3-carboxamide-1,1-dioxide This compound was prepared from 4-hydroxy-2-methyl-N-ethyl-2H-1,2-benzothiazine-3-carboxamide-1,1-dioxide, 2-amino-6-chloro-pyrazine and p-toluenesulfonic acid analogous to Example 14.
Yield: 68% of theory.
Melting point: 278°–279° C. (decomposition).
$C_{14}H_{11}ClN_4O_4S$ (366.79):
Calc.: C—45.84%; H—3.03%; Cl—9.67%; N—15.28%; S—8.74%.
Found: C—45.62%; H—3.11%; Cl—9.70%; N—15.04%; S—8.59%.

(d)
N-(6-Chloro-pyrazin-2-yl)-4-hydroxy-2-methyl-2H-1,2-benzothiazine-3-carboxamide-1,1-dioxide This compound was prepared from 4-hydroxy-2-methyl-N-cyclohexyl-2H-1,2-benzothiazine-3-carboxamide-1,1-dioxide, 2-amino-6-chloro-pyrazine and p-toluenesulfonic acid analogous to Example 14.
Yield: 68% of theory.
Melting point: 278°–279° C. (decomposition).
$C_{14}H_{11}ClN_4O_4S$ (366.79).

Calc.: C—45.84%; H—3.03%; Cl—9.67%; N—15.28%; S—8.74%.
Found: C—45.68%; H—3.04%; Cl—9.69%; N—15.12%; S—8.60%.

EXAMPLE 16

2-Ethyl-N-(6-chloro-pyrazin-2-yl)-4-hydroxy-2H-1,2-benzothiazine-3-carboxamide-1,1-dioxide 0.94 g (6 mmols) of ethyl iodide were added to a solution of 0.7 g (2 mmols) of N-(6-chloro-pyrazin-2-yl)-4-hydroxy-2H-1,2-benzothiazine-3-carboxamide-1,1-dioxide in 30 ml of methanol and 2.0 ml of 1N sodium hydroxide. The reaction mixture was stirred for 24 hours at room temperature, and was then neutralized and concentrated by evaporation in vacuo. The residue was purified by column chromatography (Merck silicagel 60, particle size 0.2–0.5 mm; eluant: chloroform/ethanol 90:10), and after recrystallization from xylene yielded 0.35 g (46% of theory) of 2-ethyl-4-hydroxy-N-(6-chloro-pyrazin-2-yl)-H-1,2-benzothiazine-3-carboxamide-1,1-dioxide. Melting point: 233°–235° C. (decomposition; from xylene).

Similar yields (between 40 and 50%) were obtained when the sodium hydroxide was replaced by potassium hydroxide, sodium methoxide or potassium tert.butoxide.

$C_{15}H_{13}ClN_4O_4S$ (380.83):
Calc.: C—47.31%; H—3.44%; N—14.71%; S—8.42%; Cl—9.31%.
Found: C—47.07%; H—3.48%; N—14.50%; S—8.40%; Cl—9.07%.

Example 17

N-(6-Chloro-pyrazin-2-yl)-4-hydroxy-2-methyl-2H-1,2-benzothiazine-3-carboxamide-1,1-dioxide This compound was prepared from N-(6-chloro-pyrazin-2-yl)-4-hydroxy-2H-1,2-benzothiazine-3-carboxamide-1,1-dioxide and methyl iodide analogous to Example 16.

Yield: 64% of theory. The yield was 43% of theory when ethanol was used as the solvent.

Melting point: 278°–279° C. (decomposition; from dioxane).

$C_{14}H_{11}ClN_4O_4S$ (366.79):
Calc.: C—45.84%; H—3.03%; N—9.67%; S—8.74%; Cl—9.67%.
Found: C—45.60%; H—3.00%; N—9.72%; S—8.70%; Cl—9.90%.

EXAMPLE 18

Ethanolamine salt of N-(6-chloropyrazin-2-yl)-4-hydroxy-2-methyl-2H-1,2-benzothiazine-3-carboxamide-1,1-dioxide A suspension of N-(6-chloro-pyrazin-2-yl)-4-hydroxy-2-methyl-2H-1,2-benzothiazine-3-carboxamide-1,1-dioxide in water was mixed with a molar equivalent of ethanolamine. The solution was consentrated by evaporation, and the residue was recrystallized from water.

Melting point: 225°–226° C. (decomposition).
$C_{16}H_{18}ClN_5O_5S$ (427.89):
Calc.: C—44.91%; H—4.24%; Cl—8.29%; N—16.37%; S—7.49%.
Found: C—45.18%; H—4.28%; Cl—8.23%; N—16.65%; S—7.42%.

The following compounds were prepared in analogy to Example 18:

Calcium salt of N-(6-chloro-pyrazin-2-yl)-4-hydroxy-2-methyl-2H-1,2-benzothiazine-3-carboxamide-1,1-dioxide.

Melting point: 246°–248° C.

Tetramethylammonium salt of N-(6-chloro-pyrazin-2-yl)-4-hydroxy-2-methyl-2H-1,2-benzothiazine-3-carboxamide-1,1-dioxide.

Melting point: 216° C. (decomposition).

Ammonium salt of N-(6-chloro-pyrazin-2-yl)-4-hydroxy-2-methyl-2H-1,2-benzothiazine-3-carboxamide-1,1-dioxide.

Melting point: 273° C. (decomposition).

Example 19

(a)

N-(6-chloro-pyrazin-2-yl)-4-hydroxy-2-methyl-2H-1,2-benzothiazine-3-carboxamide-1,1-dioxide This compound was prepared from propyl 4-hydroxy-2-methyl-2H-1,2-benzothiazine-3-carboxylate-1,1-dioxide and 2-amino-6-chloro-pyrazine analogous to Example 1.

Yield 73% of theory.
Melting point: 278°–279° C. (decomposition).
$C_{14}H_{11}ClN_4O_4S$ (366.79):
Calc.: C—45.84%; H—3.03%; Cl—9.67%; N—15.28%; S—8.74%.
Found: C—45.90%; H—3.29%; Cl—9.68%; N—15.09%; S—8.71%.

(b)

N-(6-chloro-pyrazin-2-yl)-4-hydroxy-2-methyl-2H-1,2-benzothiazine-3-carboxamide-1,1-dioxide This compound was prepared from butyl 4-hydroxy-2-methyl-2H-1,2-benzothiazine-3-carboxylate-1,1-dioxide and 2-amino-6-chloro-pyrazine analogous to Example 1.

Yield: 58% of theory.
Melting point: 278°–279° C. (decomposition).
$C_{14}H_{11}ClN_4O_4S$ (366.79):
Calc.: C—45.84%; H—3.03%; Cl—9.67%; N—15.28%; S—8.74%.
Found: C—46.01%; H—3.01%; Cl—9.60%; N—15.51%; S—8.70%.

(c)

N-(6-Chloro-pyrazin-2-yl)-4-hydroxy-2-methyl-2H-1,2-benzothiazine-3-carboxamide-1,1-dioxide This compound was prepared from benzyl 4-hydroxy-2-methyl-2H-1,2-benzothiazine-3-carboxylate-1,1-dioxide and 2-amino-6-chloro-pyrazine analogous to Example 1.

Yield: 49% of theory.
Melting point: 278°–279° C. (decomposition).
$C_{14}H_{11}ClN_4O_4S$ (366.79):
Calc.: C—45.84%; H—3.03%; Cl—9.67%; N—15.28%; S—8.74%.
Found: C—46.10%; H—3.16%; Cl—9.78%; N—15.01%; S—8.56%.

The compounds of the present invention, that is, those embraced by formula I and their non-toxic, pharmacologically acceptable salts formed with inorganic or organic bases, have useful pharmacodynamic properties. More particularly, they exhibit antithrombotic activity in warmblooded animals such as mice without any of the side effects which generally accompany antithrombotics.

The above pharmacological property was ascertained for the compounds of the present invention and two structurally related prior art compounds by the standard test methods described below, where A = N-(6-Chloro-pyrazin-2-yl)-4-hydroxy-2-methyl-2H-1,1-benzothiazine-3-carboxamide-1,1-dioxide (see Example 1);

B = Potassium salt of N-(6-chloro-pyrazin-2-yl)-4-hydroxy-2-methyl-2H-1,2-benzothiazine-3-carboxamide-1,1-dioxide (see Example 10 b);

Y = 4-hydroxy-2-methyl-N-(2-pyridyl)-2H-1,2-benzothiazine-3-carboxamide-1,1-dioxide (Piroxicam); and Z = 4-hydroxy-2-methyl-N-(2-pyrazinyl)-2H-1,2-benzothiazine-3-carboxamide-1,1-dioxide (see German Offenlegungsschrift No. 1,943,265).

The compounds were tested for their inhibiting effects in blood platelet aggregation induced by collagen and their effect of prolonging the bleeding time in mice. The compounds were also tested for their acute toxicity.

(a) Born test, collagen-induced aggregation

The thrombocyte aggregation was measured on platelet-rich plasma from healthy test subjects using the method of BORN and CROSS (J. Physiol. 170, 397 [1964]). The decrease in optical density of the platelet suspensions after the addition of collagen was measured photometrically and recorded. The rate of aggregation was deduced from the angle of inclination of the density curve. The point on the curve at which there is maximum light transmittance was used to calculate the "optical density". The quantity of collagen was selected so as to obtain an irreversible control curve.

The figures given refer to the optical density and indicate the percentage change in light transmittance (=% attenuation of aggregation) under the effect of the test substance, compared with the control.

Standard commercial collagen made by Hormon-Chemie of Munich was used.

The following Table I shows the results obtained in this test.

TABLE I

| Compound | Concentration [Mol/l] | BORN test [= % reduction in aggregation] | $IC_{50}$ [Mol/l] |
|---|---|---|---|
| A | $10^{-5}$ | 95% | $4.7 \times 10^{-7}$ |
|   | $10^{-6}$ | 71% |   |
|   | $10^{-7}$ | 6% |   |
| Y | $10^{-5}$ | 85% | $2 \times 10^{-6}$ |
|   | $10^{-6}$ | 39% |   |
| Z | $10^{-5}$ | 15% | $>1 \times 10^{-5}$ |

$IC_{50}$ = 50% reduction in aggregation

The results in Table I show that the prior art compounds Y and Z give a 50% reduction in aggregation only at a concentration of $2 \times 10^{-6}$ mol/l, or $>1 \times 10^{-5}$ mol/l, whereas compound A leads to a 50% reduction at a concentration which is about one tenth power lower.

(b) Born test, rat ex vivo, collagen-induced aggregation

The following forms were tested:

| Compound A | |
|---|---|
| Sodium salt of A = | C |
| Tetramethylammonium salt of A = | D |

-continued

| Compound B | |
|---|---|
| Ethanolammonium salt of D = | E |
| Hemicalcium salt A = | F |
| Ammonium salt of A = | G |

The test compound was administered by esophageal tube in the form of an aqueous solution or, in the case of compound A in the form of a tylose suspension, to conscious rats weighing about 450 g. After 1 hour, blood was taken from the abdominal aorta of the animals (which had previously been anesthetized with pentobarbital sodium). The platelet-rich plasma obtained by centrifuging was pooled. The controls were three animals which had not been given any of the test compound. The method of taking blood and preparing the plasma was the same for both groups. The anticoagulant used was 2% sodium citrate in a volume ratio of 1+9.

All the testing was carried out one hour after the administration of the test compound. The results are shown in the following table:

TABLE II

| Dose mg/kg p.o. | Compound | | | | | | |
|---|---|---|---|---|---|---|---|
| | A | C | D | B | E | F | G |
| 0.5 | 86% | 100% | — | — | — | — | — |
| 0.25 | 93% | 100% | — | — | — | — | — |
| 0.125 | 14% | 100% | — | — | — | — | — |
| 0.05 | — | 96% | 97% | 100% | 87% | 77% | 92% |
| 0.025 | — | 32% | 20% | 86% | 53% | 64% | 36% |
| 0.0125 | — | 0% | 27% | 26% | 10% | 27% | 7% |

Figures given indicate percentage inhibition of aggregation (measuring parameter: optical density)

All the salt forms tested had an inhibiting effect on aggregation when administered orally to rats. All the salt forms were substantially more effective than compound A. When the salts were used, about 1/5 to 1/6 of the dose of compound A was sufficient to achieve the same inhibition of aggregation.

(c) Determination of the bleeding time in mice

Method:

The bleeding time was measured on unanesthetized female mice weighing from 20 to 25 g by the method of DUKE (J. Amer. Med. Assoc.) 15, 1187, 1910). About 0.5 mm of the tip of the animals' tail was cut off, and the blood escaping was carefully wiped away with a strip of filter paper at 30 second intervals. The number of drops of blood thus obtained provided a measurement of the bleeding time. The normal bleeding time in mice is 4.1 minutes on average.

Strain of animals: NMRI Biberach
Food: Altromin R
Number of animals per test: 5

The test compound was administered by esophageal tube one hour before the measurement. The results are shown in the following table:

TABLE III

| Compound | Dose [mg/kg] | Prolongation of bleeding time |
|---|---|---|
| A | 10 | +103% |
| Y | 10 | +30% |
| Z | 10 | +62% |

As can be seen, compound A produced a 100% prolongation of the bleeding time at 10 mg/kg. At this dose, the comparison compounds X and Y already show side effects without giving a 100% prolongation of the bleeding time.

(d) Determination of acute toxicity

The acute toxicity was determined after oral administration to male and female mice. The compounds were administered as a suspension in tylose.

The following table indicates the number of animals which died within 1, 7 and 14 days after receiving the doses stated:

TABLE 4

| Compound | Dose [mg/kg] | Number of animals | Animals which died during the observation period | | |
|---|---|---|---|---|---|
| | | | 1 day | 7 days | 14 days |
| A | 250 | 10 | 0 | 0 | 0 |
| | 1000 | 10 | 0 | 0 | 0 |
| B | 250 | 5 | 0 | 0 | 0 |
| | 1000 | 5 | 0 | 1 | 1 |
| Y | 250 | 5 | 0 | 3 | 3 |
| Z | 250 | 5 | 1 | 4 | 4 |

Compounds Y and Z have a powerful antiphogistic effect, viz. in the range from 1 to 5 mg/kg p.o. in the rat (edema test), and have a strong ulcerogenic effect on the stomach of the rat. By contrast, compound A has no antiphlogistic effect in the edema test ($ED_{35} > 200$ mg/kg) and no ulcerogenic effect up to 100 mg/kg.

This absence of side effect in compound A also explains the extremely low acute toxicity ($>>1000$ mg/kg). The $LD_{50}$ values of the comparison compounds, on the other hand, were below 250 mg/kg.

For pharmaceutical purposes the compounds of the present invention are administered to warm-blooded animals perorally, parenterally or rectally as active ingredients in customary pharmaceutical compositions, that is, compositions consisting essentially of an inert pharmaceutical carrier and an effective amount of the active ingredient, such as tablets, coated pills, capsules, wafers, powders, solutions, suspensions, emulsions, syrups, suppositories and the like. An effective amount of the compounds according to the present invention is from 0.14 to 1.4 mgm/kg body weight, and the daily dose is 0.28 to 2.8 mgm/kg body weight.

The following examples illustrate a few pharmaceutical compositions comprising a compound of the present invention as an active ingredient and represent the best modes contemplated of using the invention. The parts are parts by weight unless otherwise specified.

EXAMPLE 20

Tablets

The tablet composition is compounded from the following ingredients:

| | |
|---|---|
| N—(6-Chloro-pyrazin-2-yl)-4-hydroxy-2-methyl-2H—1,2-benzothiazine-3-carboxamide-1,1-dioxide | 25.0 parts |
| Corn starch | 97.0 parts |
| Polyvinylpyrrolidone | 175.0 parts |
| Magnesium stearate | 3.0 parts |
| Total | 300.0 parts |

Preparation:

The mixture of the active ingredient and corn starch is granulated with a 14% solution of the polyvinylpyrrolidone in water through a screen with a mesh size of 1.5 mm, and the granulate is dried at 45° C. and passed through the same screen again. The granulate thus obtained is mixed with magnesium stearate and compressed into 300 mg-tablets.

EXAMPLE 21

Coated Tablets

The tablet core composition is compounded from the following ingredients:

| | |
|---|---|
| N—(6-Chloro-pyrazin-2-yl)-4-hydroxy-2-methyl-2H—1,2-benzothiazine-3-carboxamide-1,1-dioxide | 25.0 parts |
| Corn starch | 205.0 parts |
| Gelatin | 8.0 parts |
| Talcum | 18.0 parts |
| Magnesium stearate | 44.0 parts |
| Total | 300.0 parts |

Preparation:

The mixture of the active ingredient and corn starch is granulated with a 10% aqueous gelatin mixture through a screen with a mesh size of 1.5 mm, and the granulate is dried at 45° C. and passed through the same screen again. The granulate thus obtained is mixed with talcum and magnesium stearate and compressed into 300 mg-tablet cores.

The tablet cores are coated by known methods with a thin shell consisting essentially of sugar and talcum. The finished coated tablets are polished with beeswax.

EXAMPLE 22

Gelatin Capsules

The capsule filler composition is compounded from the following ingredients:

| | |
|---|---|
| N—(6-Chloro-pyrazin-2-yl)-4-hydroxy-2-methyl-2H—1,2-benzothiazine-3-carboxamide-1,1-dioxide | 25.0 parts |
| Corn starch | 365.0 parts |
| Colloidal silicic acid | 6.0 parts |
| Magnesium stearate | 4.0 parts |
| Total | 400.0 parts |

Preparation:

The ingredients are intimately admixed with each other, and 400 mg-portions of the mixture are filled into No. 1 gelatin capsules.

EXAMPLE 23

Suppositories

The suppository composition is compounded from the following ingredients:

| | |
|---|---|
| N—(6-Chloro-pyrazin-2-yl)-4-hydroxy-2-methyl-2H—1,2-benzothiazine-3-carboxamide-1,1-dioxide | 25.0 parts |
| Suppository base (e.g. cocoa butter) | 1725.0 parts |
| Total | 1750.0 parts |

Preparation:

Using an immersion homogenizer, the finely powdered active ingredient is stirred into the molten suppository base which has been cooled to 40° C. At 38° C. 1.75 g-portions of the composition are poured into slightly chilled suppository molds.

EXAMPLE 24

Suspension

The aqueous suspension is compounded from the following ingredients:

| | |
|---|---|
| N—(6-Chloro-pyrazin-2-yl)-4-hydroxy-2-methyl-2H—1,2-benzothiazine-3-carboxamide-1,1-dioxide | 0.5 parts |
| Dioctyl sodium sulfosuccinate (DONSS) | 0.02 parts |
| Benzoic acid | 0.1 parts |
| Sodium cyclamate | 0.2 parts |
| Colloidal silicic acid | 1.0 parts |
| Polyvinylpyrrolidone | 0.1 parts |
| Glycerol | 25.0 parts |
| Grapefruit flavoring | 0.1 parts |
| Distilled water q.s. ad | 100.0 parts by vol. |

Method of preparation:

The DONSS, benzoic acid, sodium cyclamate and polyvinylpyrrolidone are dissolved successively in the water which has been heated to 70° C. Glycerol and silicic acid are added thereto, the mixture is cooled to room temperature, and the finely powdered active ingredient is suspended therein by means of an immersion homogenizer. Then, the flavoring is added, and the mixture is made up to the stated volume with water. 5 ml of the suspension contain 25 mg of the active ingredient.

Any one of the other compounds embraced by formula I or a non-toxic, pharmacologically acceptable salt thereof may be substituted for the particular active ingredient in Examples 20 to 24. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

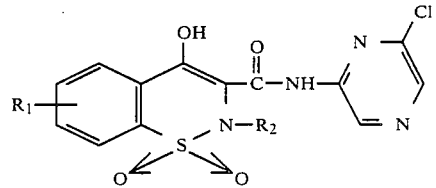

wherein
R$_1$ is hydrogen, methyl, methoxy, fluorine or chlorine; and
R$_2$ is hydrogen, methyl, ethyl or n-propyl;
or a non-toxic, pharmacologically acceptable salt thereof formed with an inorganic or organic base.

2. A compound of claim 1, which is N-(6-chloro-pyrazin-2-yl)-4-hydroxy-2-methyl-2H-1,2-benzothiazine-3-carboxamide-1,1-dioxide or a non-toxic, pharmacologically acceptable salt thereof formed with an inorganic or organic base.

3. A compound of claim 1, which is the potassium salt of a 4-hydroxy-2H-1,2-benzothiazine-3-carboxamide-1,1-dioxide of the formula of claim 1.

4. An antithrombotic pharmaceutical composition consisting essentially of an inert pharmaceutical carrier and an effective antithrombotic amount of a compound of claim 1.

5. The method of preventing or relieving thrombosis in a warm-blooded animal in need thereof, which comprises perorally, parenterally or rectally administering to said animal an effective amount of a compound of claim 1.

* * * * *

UNITED STATES PATENT AND TRADEMARK OFFICE
CERTIFICATE OF CORRECTION

PATENT NO. : 4,533,664
DATED : August 6, 1985
INVENTOR(S) : GUNTER TRUMMLITZ ET AL.

It is certified that error appears in the above-identified patent and that said Letters Patent is hereby corrected as shown below:

Column 8, line 25 --
"[methyl" should read -- methyl --.

Column 9, line 3 --
"purified column" should read -- purified by column --.

Column 10, line 21 --
"-H-1,2" should read -- 2H-1,2 --.

Signed and Sealed this

Twelfth Day of November 1985

[SEAL]

Attest:

DONALD J. QUIGG

Attesting Officer

Commissioner of Patents and Trademarks